United States Patent [19]

Roig-Greene

[11] 4,247,285

[45] Jan. 27, 1981

[54] ROOT CANAL WORKING

[76] Inventor: Jose L. Roig-Greene, Condominio San Vicente, Ste. 408, 43 Concordia St., Ponce, P.R. 00731

[21] Appl. No.: 32,265

[22] Filed: Apr. 23, 1979

[51] Int. Cl.³ .............................................. A61C 3/00
[52] U.S. Cl. .................................. 433/141; 433/159; 128/320
[58] Field of Search ...................... 128/346, 319, 320; 269/130, 131; 433/102, 224, 141, 189

[56] References Cited

U.S. PATENT DOCUMENTS

| 3,417,752 | 12/1968 | Butler | 128/346 |
| 3,955,578 | 5/1976 | Chamness | 128/320 |

Primary Examiner—Robert Peshock
Attorney, Agent, or Firm—Cushman, Darby & Cushman

[57] ABSTRACT

A method of removing an endodontic instrument fragment from a root canal, and a retrieving assembly for practicing the method. A wire is formed into a loop having two free ends opposite the loop. The free ends of the wire are passed through an elongated tube so that the loop extends from one side of the tube and the free ends extend from the opposite side of the tube. The loop is bent so that it makes a positive angle with respect to the tube, and the loop and a portion of the tube are inserted into the root canal alongside the fragment. The loop is slid passed the fragment so that the closed portion of the loop is on the opposite side of the fragment than the tube, and then the free ends of the wire are gripped with a hemostat and the hemostat is rotated about an axis perpendicular to the direction of elongation of the tube, to cause the loop and tube to tightly hold the fragment. Then the tube and loop, with tightly held fragment, are withdrawn from the root canal.

13 Claims, 7 Drawing Figures

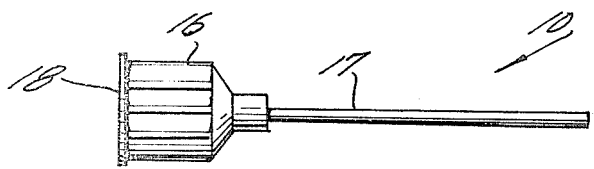
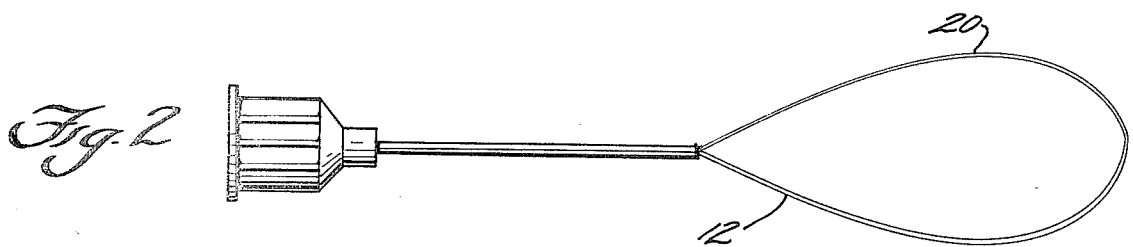
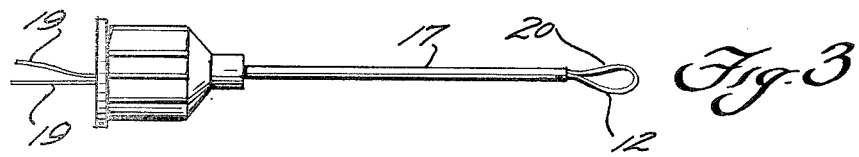
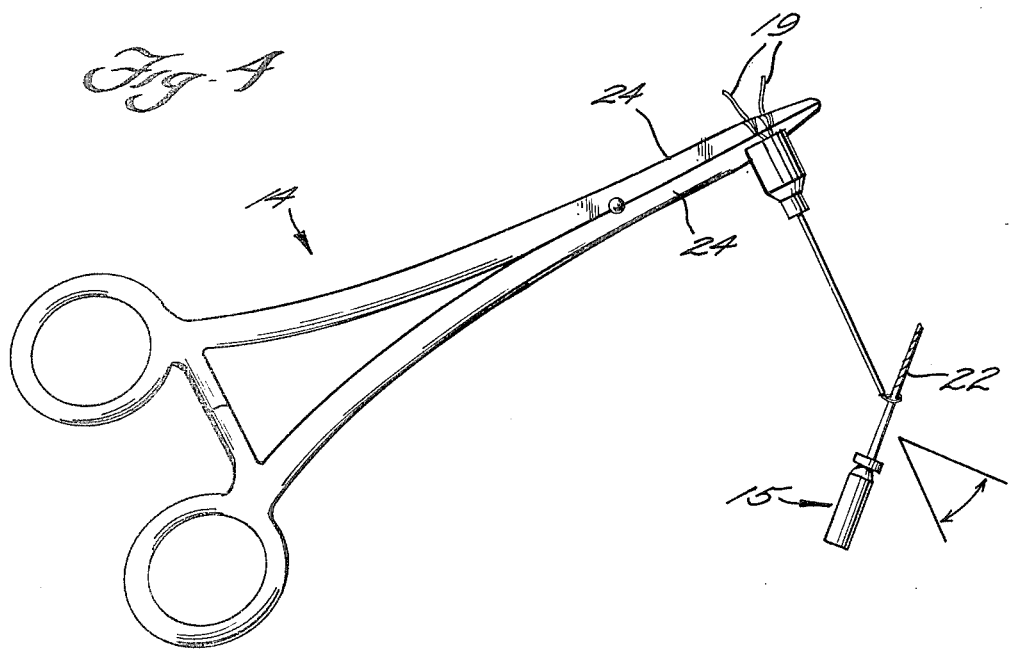

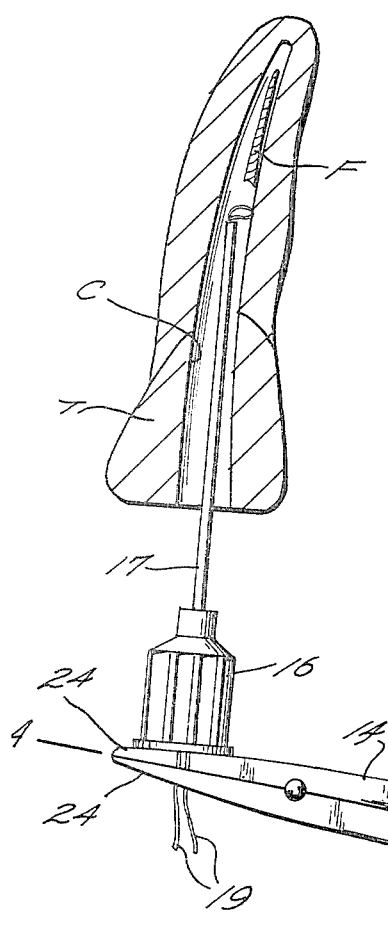
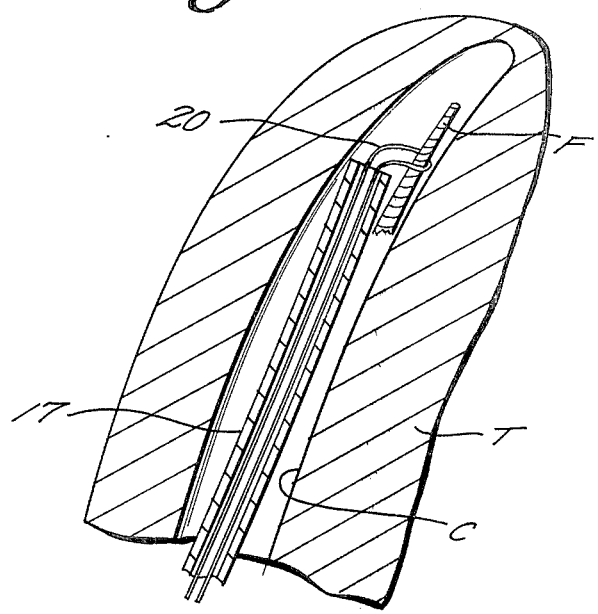
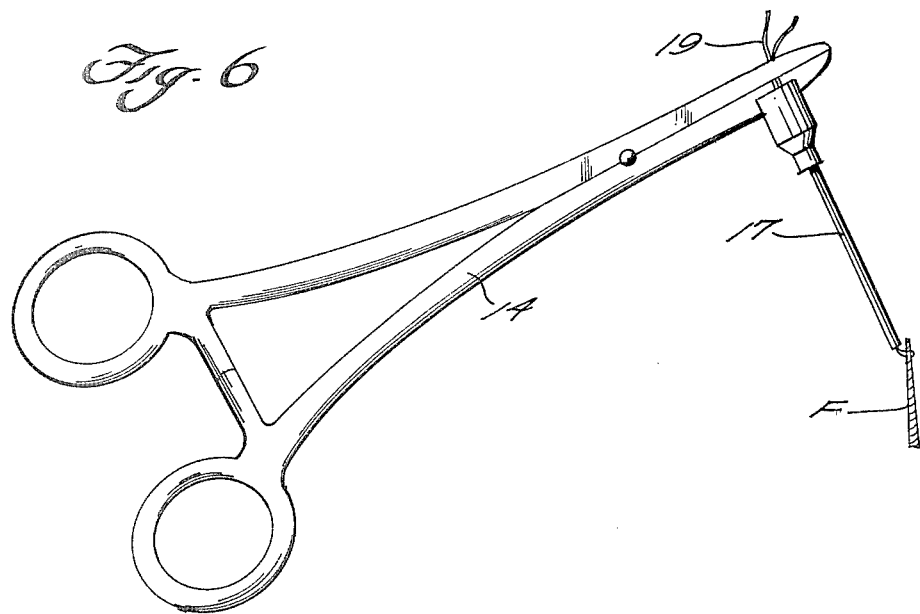

ROOT CANAL WORKING

BACKGROUND AND SUMMARY OF THE INVENTION

The invention relates to a method, and an assembly for practicing the method, for removing endodontic instrument fragments or the like from root canals. As is well known, the endodontic treatment conventionally contemplates appropriate dressing of the access cavity to the root-pulp channel with removal of pulp in the cavity; location of the opening of the radicular channels and measuring the depth thereof; removal of radicular contents and organic waste to the apex with cleansing by introducing suitable chemical solutions; and channel drying and tridimensional filling thereof. During practice of the endodontic treatment, foreign objects are often located or left in the root canal, such as fragments of root canal instruments (such as barbed broaches, reamers, files and rotary burs), obturating material such as silver cones and gutta percha; condenser points, lentulo spirals, pins and posts. While solvents can penetrate root canals obstructed by some foreign objects, and silver points can be removed with conventional instruments, some foreign objects—such as fragments of endodontic instruments—are difficult to remove with conventional root canal pliers, silver point retrievers, or other conventional structures. Difficulties especially ensue where an instrument breaks before completion of the bio-mechanical preparation of the canal since in such circumstances enlightened technique requires removal of the fragment before filling.

In addition to the use of solvents, silver point retrievers, and root canal pliers, prior art techniques for foreign object removal have included the introduction of a broach wrapped in cotton into the canal in the hopes that the fragment will become enmeshed in the cotton. Other proposals include the use of splinter forceps, rasps with sharp cutting edges, and the use of trepan burs to remove the tooth structure around the fragment so that an extractor can be introduced to grasp the end of the fragment to remove it. While such techniques are often successful, they may require the removal of some essential root structure, are time consuming, are difficult to utilize in anything besides straight canals, and require relatively expensive equipment.

According to the method and apparatus of the present invention, the extraction of endodontic instrument fragments or the like is substantially simplified, a method being provided that has broad applicability, is useful both in straight and curved canals, is not particularly time consuming, does not require the removal of essential root structure, and employs very inexpensive components.

The method according to the present invention utilizes a wire and an elongated tube. The wire is formed into a loop and a free end of the wire is passed through the tube so that the loop extends from one side of the tube and the free end extends from the opposite side of the tube. The loop and a portion of the tube are inserted into the root canal alongside the fragment, in a clear area between the fragment and the canal wall. The loop is slid past the fragment so that the closed portion of the loop is on the opposite side of the fragment than the tube, a force is exerted on the wire free end sufficient to cause the loop and tube to tightly hold the fragment, and the tube and loop—with tightly held fragment—are withdrawn from the root canal. If it is necessary to form the clearance alongside the fragment, the clearance formation can be accomplished without the removal of essential tooth structure since only a small portion of the tooth structure or other material alongside the fragment need be removed. Preferably both free ends of the wire pass through the tube, and are gripped at the ends thereof opposite the loop by a mosquito hemostat or the like, which is rotated about an axis perpendicular to the direction of elongation of the tube to effect tightening of the wire on the fragment.

The loop is set for introduction into the root canal by placing an object in the loop having a larger cross-sectional area than that of the fragment; placing the object at about a 45° angle with respect to the tube; exerting a force on the wire free end sufficient to cause tightening of the loop around the object; and removing the object from the loop. The elongated tube may be formed from a disposable dental injector needle having a hub with the hollow needle extending through the hub on both sides thereof with a bevel cut on the most distal end of the needle. The needle is cut off just before the bevel cut and so that it is substantially flush with the hub on the end thereof opposite the bevel cut.

The retrieving assembly according to the present invention is very inexpensive, comprising a wire, an elongated tube having a cross-sectional area greater than the cross-sectional area of the wire, and a clamping means (such as a mosquito hemostat) for securely clamping the wire ends for effecting movement of the wire with respect to the tube. Preferably an elongated hub is formed at one end of the tube, and the tube is flexible.

It is the primary object of the present invention to provide a versatile, simple, inexpensive method and assembly for retrieving foreign objects from root canals. This and other objects of the invention will become clear from an inspection of the detailed description of the invention, and from the appended claims.

BRIEF DESCRIPTION OF THE DRAWINGS

FIG. 1 is a plain view of an exemplary tube and wire for use in practicing the present invention; and FIGS. 2-6 are schematic views illustrating a step-by-step removal of an endodontic instrument fragment from a root canal as according to the method of the present invention, FIG. 5b being an enlargement of the fragment area of FIG. 5a.

DETAILED DESCRIPTION OF THE DRAWINGS

The retrieving assembly according to the present invention includes an elongated tube 10, a wire 12, and a clamping means, such as a mosquito hemostat 14. The tube 10 preferably includes a flexible elongated shaft portion 17, and a hub 16 substantially flush with the end 18 of the tube 10. The tube 10 may conveniently be formed by taking a 25 gauge disposable dental injector needle, severing it just before the bevel cut thereof, and severing the end opposite the bevel cut so that it is substantially flush with the hub 16 (forming end 18). The wire 12 is preferably a 5 or 6 inch segment of steel wire, such as the smooth wire provided in a 27 pound test SEVENSTRAND brand fishing leader wire.

In practicing the method of the invention, a loop 20 is formed in the wire 12, and the free ends 19 of the wire opposite the loop 20 are introduced into the flexible shaft 17 [FIG. 2], and are pushed through until the ends 19 extend through the end 18 of the tube 10 [FIG. 3]. The loop 20 extending past the end of the shaft 17 is then bent to form a positive angle between it and the shaft 17, this preferably being accomplished by placing a root canal file (or other object) two numbers larger than the known (or estimated) fragment through the loop 20, exerting a force on the wire free ends 19 (as with the hemostat 14 clasping the ends 19 between the jaws 24 thereof) to tighten the loop 20 around the file 22 and then placing the file 22 at about a 45° angle with respect to the tube shaft 17. Then the file 22 is removed from the loop 20. [See FIG. 4].

If sufficient clearance is provided between the fragment F and the canal C wall of the tooth T [see FIGS. 5a and 5b], the loop 20 is then inserted into the canal C. However, where insufficient clearance is provided, clearance formation is accomplished without the removal of essential tooth structure by reaming and/or filing of the root canal just alongside the fragment F, there being no necessity for removing a large diameter area of the tooth T around the proximate end of the fragment F. A small round bur may be utilized to prepare a groove around the fragment F to facilitate placing the wire loop 20.

Once sufficient clearance is provided, the loop 20 and a portion of the tube 10 (the front of the shaft 17) are inserted into the canal C alongside the fragment F, the flexible nature of the shaft 17 allowing the assembly according to the invention to then slid passed the fragment F so that the closed portion of the loop 20 is on the opposite side of the fragment F as the tube shaft 17 [See FIG. 5b] and then a force is exerted on the wire free ends 19 sufficient to cause the loop 20 and tube shaft 17 to tightly hold the fragment F.

The necessary force is exerted on the wire ends 19 to cause the wire 12 to tighten around the fragment F by gripping the free ends 19 with the jaw portions 24 of the hemostat 14, and then rotating the hemostat 14 about an axis A—A [See FIG. 5a] against the tube hub 16, the axis A—A being generally perpendicular to the direction of elongation of the tube shaft 17. The tightly held fragment F is then removed by carefully pulling on the hemostat 14 to withdraw the shaft 17 from the root canal C. The wire is unlikely to slip off the fragment F while removal is attempted, and if the wire 12 should snap as a result of the application of excessive pressure, another wire is readily provided in its place. In situations where the fragment F is not readily visible, radiographs of the root canal area are taken at various stages of the procedure to insure that the loop 20 is properly in place with respect to the fragment F before extraction is attempted.

While the method according to the present invention has been primarily described with respect to fractured endodontic instruments such as barbed broaches, reamers, files, rotary burs and the like, it is also applicable to the removal of other foreign objects such as silver cones, gutta percha, condenser points, lentulo spirals, pins, posts and the like. The term "endodontic instrument fragment or the like" is to be interpreted to cover such objects.

It will be seen that according to the present invention a method, and an associated apparatus assembly, have been provided which facilitate the ready removal of endodontic instrument fragments or the like from a root canal area, being applicable to a wide variety of situations and objects and root canal shapes, and effecting removal in an inexpensive manner and in most cases without requiring removal of essential root structure. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and assemblies.

What is claimed is:

1. A retrieving assembly comprising: a wire; a mosquito hemostat having elongated jaws for clamping the wire; and an elongated tube having a cross-sectional area greater than the cross-sectional area of said wire, and having a hub formed at one end thereof, and said hub having a width dimension extending perpendicular to the dimension of elongation of said tube, and said width being less than the length of said jaws but great enough to support said jaws on said hub for rotation of said jaws with respect to said hub about an axis perpendicular to the dimension of elongation of said tube.

2. An assembly as recited in claim 1 wherein said wire extends through said tube so that a loop is formed in said wire at one end of said tube, and two wire free ends extend from the other end of said tube, said tube cross-sectional area being at least twice as great as that of said wire.

3. An assembly as recited in claim 1 wherein said elongated tube is flexible.

4. A method of removing an endodontic instrument fragment or the like from a root canal, utilizing a wire, and an elongated tube, wherein clearance is provided between the fragment and the canal wall along the side of the fragment, said method comprising the steps of:
   (a) forming the wire into a loop;
   (b) passing a free end of the wire through the tube so that the loop extends from one side of the tube and the free end extends from the opposite side of the tube;
   (c) inserting the loop and a portion of the tube into the root canal alongside the fragment;
   (d) sliding the loop past the fragment so that the closed portion of the loop is on the opposite side of the fragment than the tube;
   (e) exerting a force on the wire free end sufficient to cause the loop and the tube to tightly hold the fragment; and
   (f) withdrawing the tube and loop, with held fragment, from the root canal.

5. A method as recited in claim 4 wherein step (a) is accomplished by forming the wire into a loop at a center portion thereof and having two free ends opposite the loop; and wherein step (b) is accomplished by passing both free ends of the wire through the tube so that both free ends extend from the opposite end of the tube as the loop; and wherein step (e) is accomplished by exerting a force on both free ends of the wire.

6. A method as recited in claim 4 comprising the further step of, in conjunction with steps (c) and (d), taking radiographs of the root canal area to insure that the loop is properly in place with respect to the fragment before practicing step (e).

7. A method as recited in claim 5 wherein the tube is flexible, and further utilizing a hemostat or like clamping structure; and wherein step (e) is accomplished by gripping the wire free ends with the hemostat, and rotating the hemostat about an axis generally perpendicular to the direction of elongation of the tube.

8. A method as recited in claim 7 wherein the tube has a hub formed adjacent the end thereof through which the wire free ends pass, and wherein step (e) is further accomplished by rotating the hemostat against the tube hub.

9. A method as recited in claim 5 comprising the further step of
   (h) between steps (b) and (c), bending the loop extending past the tube end with which it is associated to form a positive angle between the loop and the tube.

10. A method as recited in claim 9 wherein step (h) is accomplished by bending the loop to have an angle of about 45° with respect to the tube, said bending being accomplished by placing an object having a larger cross-sectional area than that of the fragment through the loop; exerting force on the wire free ends sufficient to cause tightening of the loop around the object; placing the object at about a 45° angle with respect to the tube; and removing the object from the loop.

11. A method as recited in claim 4 comprising the further step of forming the elongated tube from a disposable dental injector needle having a hub, a hollow needle extending through the hub on both sides thereof with a bevel cut on the most distal end of the needle; said forming being accomplished by cutting off the needle just before the bevel cut, and cutting off the needle so that it is substantially flush with the hub on the end thereof opposite the bevel cut.

12. A method as recited in claim 4 comprising the further step of
   (g) before step (c), forming the clearance alongside the fragment, clearance formation being accomplished without the removal of essential root structure.

13. A method as recited in claim 12 wherein step (g) is accomplished by reaming and/or filing, of the root canal.

* * * * *